(12) United States Patent
Babich

(10) Patent No.: US 7,556,794 B2
(45) Date of Patent: *Jul. 7, 2009

(54) PENDANT FATTY ACID IMAGING AGENTS

(75) Inventor: John W. Babich, North Scituate, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/599,159

(22) Filed: Nov. 13, 2006

(65) Prior Publication Data

US 2007/0128119 A1 Jun. 7, 2007

Related U.S. Application Data

(63) Continuation of application No. 10/405,094, filed on Apr. 1, 2003, now Pat. No. 7,179,444.

(60) Provisional application No. 60/368,933, filed on Apr. 1, 2002.

(51) Int. Cl.
*A61K 51/00* (2006.01)
*A61M 36/14* (2006.01)

(52) U.S. Cl. .................. 424/1.65; 424/1.11; 424/1.37; 534/14

(58) Field of Classification Search ............... 424/1.11, 424/1.37, 1.65, 1.53, 1.73, 9.1; 554/1; 562/606
See application file for complete search history.

(56) References Cited

U.S. PATENT DOCUMENTS

| | | | | |
|---|---|---|---|---|
| 4,524,059 | A * | 6/1985 | Elmaleh et al. | 424/1.81 |
| 4,615,876 | A | 10/1986 | Troutner et al. | 424/1.1 |
| 4,746,505 | A | 5/1988 | Jones et al. | 424/1.1 |
| 5,538,712 | A * | 7/1996 | Wenzel et al. | 424/1.45 |
| 6,437,103 | B1 * | 8/2002 | Babich et al. | 534/14 |
| 7,005,119 | B2 * | 2/2006 | Elmalch | 424/1.69 |
| 7,060,251 | B1 * | 6/2006 | Elmaleh et al. | 424/9.4 |
| 7,179,444 | B2 * | 2/2007 | Babich | 424/1.65 |

FOREIGN PATENT DOCUMENTS

| EP | 1 046 401 A2 | 10/2000 |
|---|---|---|
| WO | 9719705 | * 6/1997 |
| WO | WO 97/19705 | 6/1997 |
| WO | WO 00/61196 | 10/2000 |

OTHER PUBLICATIONS

Alberto et al.; "A Novel Organometallic Aqua Complex of Technetium for the Labeling of Biomolecules: Synthesis of [$^{99m}$Tc(OH$_2$)$_3$(CO)$_3$]$^+$ from [$^{99m}$TcO$_4$]- In Aqueous Solution and Its Reaction with a Bifuctional Ligand", J. Am. Chem. Soc. 120: 7987-7988, (1988).

Goodman et al.; "Synthesis and Evaluation of Radioiodinated Terminal p-Iodophenyl-Substituted α- and β-Methyl-Branched Fatty Acids"; J. Med. Chem. 27: 390-397, (1984).

Jones et al.; "7,10 Bis (2-Mercapto-2-Methyl) Propyl-7,10-Diazapalmitic Acid: A Novel, N$_2$S$_2$ Ligand for Technetium-99m", Bioorganic & Medicinal Chemistry Letters, 6(20): 2399-2404, (1996).

Lee et al.; "Synthesis and Evaluation of Cyclopentadienyl Tricarbonyl $^{99m}$Tc Hexadecanoic Acid For Myocardial Imaging", Journal of Nuclear Medecine, 42(5): 260P, (May 2001).

Lee et al.; "Cyclopentadienyl Tricarbonyl Technetium-99m Octanoic Acid: A Novel Radiotracer for Evaluation of Fatty Acid Metabolism in the Liver", J. Labelled Cpd Radiopharm. 44 (suppl. 1): S535-S535, (2001).

Magata et al.; "$^{99m}$Tc- Labeled Long Chain Fatty Acid Derivative for Myocardial Imaging", Journal of Nuclear Medicine, 42(5): Suppl. P. 260P (May 2001).

Rattat et al.; "Dicarbonyl-Nitrosyl-Complexes of Rhenium (Re) and Technetium (Tc), A Potentially New Class of Compounds for the Direct Radiolabeling of Biomolecules", Cancer Biotherapy & Radiopharmaceuticals, 16(4):339-343, (Nov. 4, 2001).

Yamamura et al.; "Technetium-99m-Labeled Medium Chain Fatty Acid Analogues Metabolized by β-Oxidation: Radiopharmaceutical for Assessing Liver Function", Bioconjugate Chem. 10: 489-495, (1999).

International Search Report Completed on Jul. 18, 2003 and Mailed on Aug. 5, 2003.

* cited by examiner

*Primary Examiner*—D. L Jones
(74) *Attorney, Agent, or Firm*—Foley & Lardner LLP; Michel Morency; James F. Ewing

(57) ABSTRACT

The disclosure provides pendant fatty acid compounds for use in diagnostic imaging, (particularly the cardiovascular system), as well as kits comprised of the same. The disclosure also provides for a method administering a imaging agent with a high specificity for the myocardium.

8 Claims, 4 Drawing Sheets

PENDANT FATTY ACID IMAGING AGENTS

RELATED APPLICATION INFORMATION

This application is a continuation application of and claims priority to and the benefit of U.S. patent application Ser. No. 10/405,094 filed on Apr. 1, 2003 now U.S. Pat. No. 7,179,444, which claims priority to U.S. Provisional Patent Application No. 60/368,933 filed Apr. 1, 2002, the entire teachings of which are incorporated herein by reference.

BACKGROUND

Every year, seven million Americans arrive in emergency rooms complaining of chest pain indicating a possible heart attack. Identifying which patients are actually having a heart attack and require hospitalization can be challenging. More than 40% of emergency room chest pain patients, estimated at more than 3 million, are admitted to hospitals unnecessarily at an estimated annual cost of $10-$13 billion. These unnecessary hospitalizations may be avoided if better diagnostic tests existed for emergency room use. As pointed out in the NIH's 1997 National Heart Attack Alert Program Report on Diagnostic Technologies for Acute Cardiac Ischemia, there have been no diagnostic tests to-date that have been shown by controlled clinical trials to improve emergency room decision-making in actual practice. Unstable angina is also part of the population arriving at the emergency room. Approximately 6 out of 10,000 individuals suffer from unstable angina, or approximately 150,000 Americans.

Fatty acids are the primary source of energy for the heart muscle under normal conditions of blood flow and oxygen delivery. In ischemia, when blood flow is diminished under stress, the heart lacks an adequate supply of oxygen to utilize fatty acids efficiently. Instead, the heart shifts from fatty acid metabolism to glucose. This change occurs immediately after heart muscle ischemia. Hence, a radiolabeled fatty acid would be of value for clinical evaluation of ischemic heart disease and cardiomyopathies.

There have been numerous attempts to measure fatty acid metabolism in the heart using radiolabeled fatty acids. Although C-11 labeled fatty acids are a true tracer for fatty acids, the complicated metabolic profile and consequent pharmacokinetic modeling has kept it from being applied widely. Many fatty acids have been radiolabeled, but those that are metabolically trapped are superior to those that are metabolized. This may be analogous to a situation with 2-fluoro-2-deoxyglucose (FDG), a glucose analog, which is a more widely used than C-11 glucose because metabolic trapping leads to easier analysis by virtue of the simpler pharmacokinetic modeling. Other fatty acids have been used, for example, BMIPP ((15-p-iodophenyl)-methylpentadecanoic acid). BMIPP is an 123-iodine labeled fatty acid analog for imaging heart disease using conventional nuclear medicine cameras. BMIPP may be used to image ischemic areas of the heart soon after the ischemic event and has the added value of being able to image the ischemic muscle even several days after injury to the myocardium.

Radiolabeled fatty acids may be useful in evaluating the efficacy of beta-blocker therapy in patients with dilated cardiomyopathy (DCM) and ACE inhibitor therapy in congestive heart failure patients. These radiolabeled fatty acids have been shown to demonstrate clinical utility in the evaluation of cardiac disease, including acute myocardial infarction (AMI), unstable angina (UA), prediction of functional recovery of ischemic myocardium, prediction of future cardiac events, and assessment of therapy in patients with heart failure.

A metabolically blocked radiolabeled fatty acid may be a superior tracer to catabolizable fatty acid and therefore a Tc-99m labeled fatty acid may be of greater value than known labeled fatty acids. Early attempts to label fatty acids with Tc-99m resulted in radiopharmaceuticals that were not true fatty acid tracers. These attempts by other investigators have, in general, been directed at omega-labeled fatty acids. However, none of the omega labeled fatty acids have been shown to trace fatty acid metabolism, while some had either low heart-to-blood ratios and others exhibited low uptake in the myocardium.

SUMMARY

The present disclosure provides novel radiopharmaceutical agents for diagnostic imaging. The imaging agents of the disclosure are radionuclide containing analogs of fatty acids and are particularly suitable for cardiovascular imaging.

In one aspect, the imaging agent comprises a compound represented by the formula:

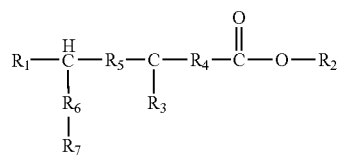

wherein:

$R_1$, $R_4$, $R_5$, and $R_6$ are each independently selected from an alkyl, alkenyl or a bond;

$R_2$ is selected from the group consisting of a hydrogen, a primary amine, a secondary amine, a tertiary amine, an alkyl group, a substituted alkyl group, an aryl group, and a substituted aryl group;

$R_3$ is selected from the group consisting of a hydrogen, an alkyl, a substituted alkyl, a hydroxyl, a keto ester, an alkoxy, a halide, and an amine;

$R_7$ is selected from a metal chelating moiety bound to a metallic carbonyl ligand; and the stereochemical configuration of a compound represented by 1 may be R or S at the stereocenters; or a mixture of these configurations, and the pharmaceutically acceptable salts, esters, amides, and prodrugs thereof.

In an embodiment, a composition is provided that comprises compound 1; wherein the compound is a R stereoisomer, and the composition is of more than about 75% isomeric purity. In another embodiment, a composition is provided that comprises compound 1; wherein the compound is a S stereoisomer, and the composition is of more than about 75% isomeric purity.

In an embodiment, $R_3$ is a methyl group or $CF_3$. In another embodiment, $R_3$ is bound to the C-3 position relative to the carboxyl end of compound 1. In yet another embodiment, $R_3$ is bound to the C5, C7 or C9 position. In an embodiment, the metallic carbonyl ligand is a radionuclide carbonyl compound.

In another embodiment, $R_7$ is selected from a metal chelating moiety bound to a metallic carbonyl ligand wherein the metallic carbonyl ligand comprises a low oxidation state metal. In yet another embodiment, the metallic carbonyl ligand is a $^{99m}$Tc-carbonyl compound or rhenium carbonyl compound. In yet another embodiment, the metallic carbonyl ligand is a $^{99m}$Tc-tricarbonyl compound or a rhenium tricarbonyl compound.

In another aspect, the imaging agent comprises the compound represented by the formula:

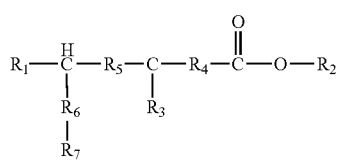

2 wherein $R_1$, $R_4$, $R_5$, and $R_6$ are each independently selected from an alkyl, alkenyl or a bond;

$R_2$ is selected from the group consisting of a hydrogen, a primary amine, a secondary amine, a tertiary amine, an alkyl group, a substituted alkyl group, an aryl group, and a substituted aryl group;

$R_3$ is selected from the group consisting of a hydrogen, an alkyl, a hydroxyl, a keto ester, an alkoxy, a halide, and an amine;

$R_7$ is selected from:

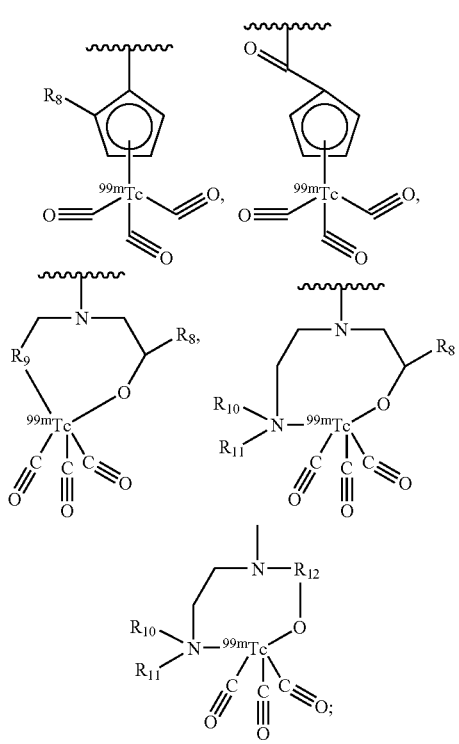

$R_8$ is selected from the group O, H, OH, alkoxy, or O-alkyl;
$R_9$ is any heterocycle;
$R_{10}$ and $R_{11}$ are each independently selected from the group of hydrogen, alkyl or substituted alkyl;
$R_{12}$ is selected from the group of aryl, alkyl, or heterocycle; the stereochemical configuration of a compound represented by 2 may be R or S, at the stereocenters; or a mixture of these configurations, and the pharmaceutically acceptable salts, esters, amides, and prodrugs thereof.

In an embodiment, $R_3$ is selected from a methyl group or a substituted methyl group. In another embodiment $R_3$ is $CH_3$ or $CF_3$. In another embodiment, $R_3$ is bound to the C-3 position relative to the carboxyl end of compound 2. In yet another embodiment, $R_3$ is bound to the C5, C7, or C9 position.

In another embodiment, $R_8$ is O.

In another aspect, the disclosure provides an imaging agent comprising the compound represented by:

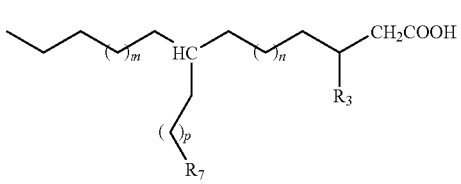

3 wherein $R_3$ is H or alkyl;
$R_7$ is selected from

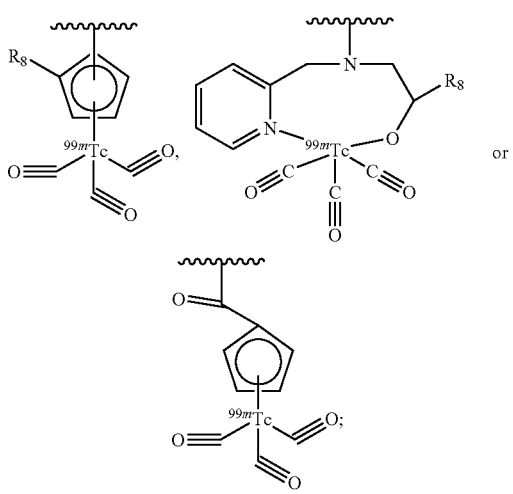

$R_8$ is selected from the group consisting of O, H, OH, alkoxy, or O-alkyl;

m is an integer between 0 and 12 inclusive;

n is an integer between 0 and 12 inclusive;

p is an integer between 0 and 12 inclusive; and the stereochemical configuration of a compound represented by 3 may be R or S, at the stereocenters; or a mixture of these configurations, and the pharmaceutically acceptable salts, esters, amides, and prodrugs thereof.

In one embodiment, $R_8$ is O.

In another aspect, the imaging agent comprises a compound represented by the formula:

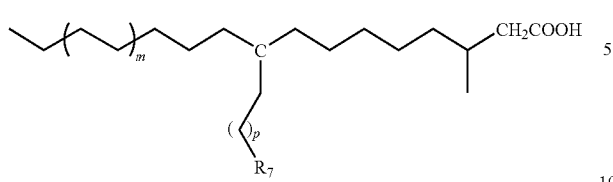

wherein:

$R_7$ is selected from

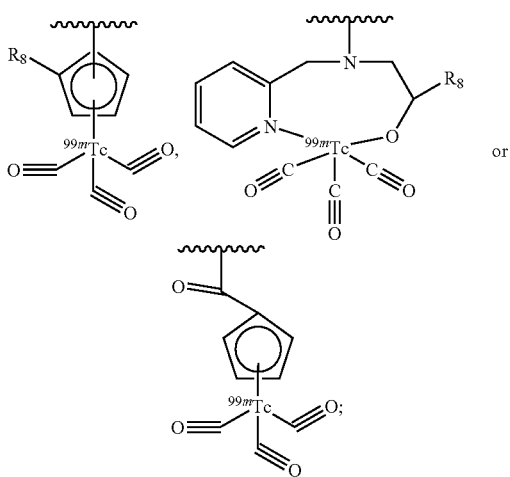

$R_8$ is selected from the group O, H, OH, alkoxy, or O-alkyl;

m is an integer selected from 0 to 12;

p is an integer selected from 0, 1, 2, 4, 6 or 8; and the stereochemical configuration of a compound represented by 4 may be R or S, at the stereocenters; or a mixture of these configurations, and the pharmaceutically acceptable salts, esters, amides, and prodrugs thereof.

In one embodiment, m is an integer selected from 0, 1 or 2. In another embodiment, $R_8$ is O.

In another aspect the disclosure provides methods for using imaging agents to identify a lesion. In an embodiment, the lesion is in a cardiovascular system. In an exemplary embodiment, the detection of the lesion may be used in diagnosing or effectively treating myocardial infarction, unstable angina, heart failure, and ischemic myocardium. In an embodiment, the compounds of the instant disclosure have high specificity for the myocardium when administered to a subject in vivo. The fatty acid complex disclosed herein may show a heart to blood ratio of at least about 3 to 1 and at least about 0.3% ID/g heart retention within about 60 min of administration. The disclosure also provides for a method of identifying a cardiovascular lesion comprising: administering an imaging agent to a subject; wherein said imaging agent shows a heart to blood ratio of at least about 3 to 1 and at least about 0.3% ID/g heart retention within about 60 minutes of administration.

A further aspect of this disclosure contemplates kits including subject compounds and a pharmaceutically acceptable carrier, and optionally instructions for their use. Uses for such kits include therapeutic management and medical imaging applications.

These and further embodiments of the present disclosure, and their features and characteristics will be apparent from the following description, drawings, and claims.

DETAILED DESCRIPTION

1. Overview

Figure 1:
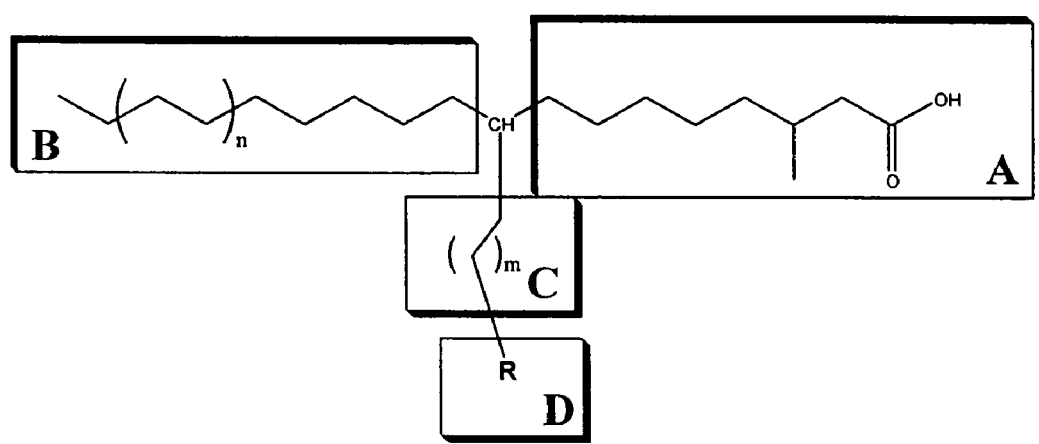
FIG. 1 depicts a compound of the present disclosure.
Figure 2:
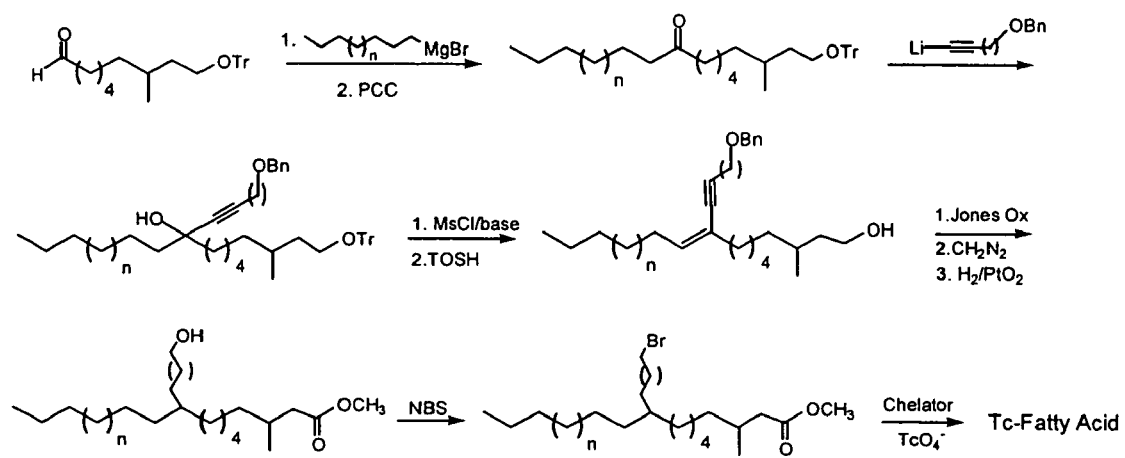
FIG. 2 depicts a synthetic route to compounds of the present disclosure.

In general, the present disclosure is based on the identification of compounds that may be useful for medical imaging. The compounds comprise a metal chelating agent bound to a radionuclide carbonyl ligand, which is pendantly bound to a fatty acid. The compounds may be particularly useful for monitoring alterations in fatty acid metabolism or utilization.

2. Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In an embodiment, a straight chain or branched chain alkyl has 30 or fewer carbon atoms in its backbone (e.g., $C_1$-$C_{30}$ for straight chain, $C_3$-$C_{30}$ for branched chain), and in one embodiment, 20 or fewer. Likewise, cycloalkyls have from 3-10 carbon atoms in their ring structure, and in one embodiment, have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, and in one embodiment, from one to six carbon atoms in its backbone structure. Likewise, "lower alkenyl" and "lower alkynyl" have similar chain lengths. In an embodiment, alkyl groups are lower alkyls. In an embodiment, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The term "heteroatom" as used herein means an atom of any element other than carbon or hydrogen. Exemplary heteroatoms are boron, nitrogen, oxygen, phosphorus, sulfur and selenium.

The terms "heterocyclyl" or "heterocyclic group" refer to 3- to 10-membered ring structures, and in one embodiment, 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

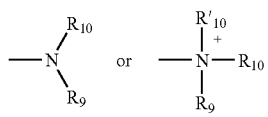

wherein $R_9$, $R_{10}$ and $R'_{10}$ each independently represent a group permitted by the rules of valence.

The term "acylamino" is art-recognized and refers to a moiety that can be represented by the general formula:

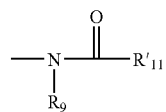

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

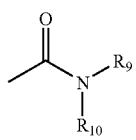

wherein $R_9$, $R_{10}$ are as defined above. In an exemplary embodiment an amide will not include imides which may be unstable.

The term "carbonyl" is art recognized and includes such moieties as can be represented by the general formula:

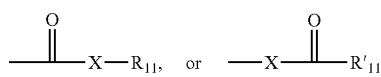

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and non-aflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, $2^{nd}$ ed.; Wiley: New York, 1991).

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as precursors), wherein one or more simple variations of substituents are made which do not adversely affect the efficacy of the compound to function as precursors of radiolabelled compounds. In general, the compounds of the present disclosure may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this disclosure, the chemical elements are identified in accordance with the Periodic Table of the Elements, CAS version, Handbook of Chemistry and Physics, 67th Ed., 1986-87, inside cover. Also for purposes of this disclosure, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material, involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.,* 66:1-19 (1977).

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

A "radionuclide" refers to molecule that is capable of generating a detectable image that can be detected either by the naked eye or using an appropriate instrument, e.g. positron emission tomography (PET), and single photon emission tomography (SPECT). Radionuclides useful within the present disclosure include penetrating photon emitters including gamma emitters and X-ray emitters. These rays accompany nuclear transformation such as electron capture, beta emission and isomeric transition. Radionuclides useful include those with photons between 80 and 400 keV and positron producers, 511 keV annihilation photons and acceptable radiation doses due to absorbed photons, particles and half life. Radionuclides include radioactive isotopes of an element. Examples of radionuclides include $^{123}$I, $^{125}$I, $^{99m}$Tc, $^{18}$F, $^{68}$Ga, $^{62}$Cu, $^{111}$In, $^{131}$I, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{67}$Ga, $^{94}$Tc, $^{105}$Rh, $^{95}$Ru, $^{177}$Lu, $^{170}$Lu $^{11}$C, and $^{76}$Br.

A "subject" shall mean a human or animal e.g. a non-human mammal (e.g. rat, mouse, cat, dog, horse, sheep, cow, monkey), avian, or amphibian.

3. Compounds

In one aspect, the imaging agent comprises a compound represented by the formula:

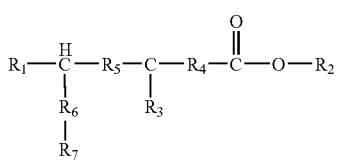

(1)

wherein $R_1$, $R_4$, $R_5$, and $R_6$ are each independently selected from an alkyl, alkenyl or a bond;

$R_2$ is selected from the group consisting of a hydrogen, a primary amine, a secondary amine, a tertiary amine, an alkyl group, a substituted alkyl group, an aryl group, and a substituted aryl group;

$R_3$ is selected from the group consisting of a hydrogen, an alkyl, a substituted alkyl, a hydroxyl, a keto ester, an alkoxy, a halide, and an amine;

$R_7$ is selected from a metal chelating moiety bound to a metallic carbonyl ligand; wherein a stereochemical configuration of a compound represented by 1 may be R or S at the stereocenters; or a mixture of these configurations, and the pharmaceutically acceptable salts, esters, amides, and prodrugs thereof.

In an embodiment, a composition is provided that comprises compound 1; wherein the compound is a R stereoisomer, and the composition is of more than about 75%, more than about 80%, or even more than about 90% isomeric purity. In another embodiment, a composition is provided that comprises compound 1; wherein the compound is a S stereoisomer, and the composition is of more than about 75% more than about 80%, or even more than about 90% isomeric purity. In an exemplary embodiment, the purity of composition comprising a stereoisomer is such that the desired heart to blood ratio, or heart intake, is obtained.

In an embodiment, $R_3$ is a methyl group or $CF_3$. In another embodiment, $R_3$ is bound to the C-3 position relative to the carboxyl end of compound 1. In yet another embodiment, $R_3$ is bound to the C5, C7 or C9 position. In an embodiment, the metallic carbonyl ligand is a radionuclide carbonyl compound.

In an embodiment, the metallic carbonyl ligand is a radionuclide carbonyl compound. In another embodiment, $R_7$ is selected from a metal chelating moiety bound to a metallic carbonyl ligand wherein the metallic carbonyl ligand comprises a low oxidation state metal. In a further embodiment, the radionuclide carbonyl compound is a $^{99m}$Tc-carbonyl compound. In another further embodiment, the radionuclide carbonyl compound is a $^{99m}$Tc-tricarbonyl compound. In one embodiment, the metallic carbonyl compound is rhenium-carbonyl compound.

Any suitable metal chelating moiety or structure may be used to provide a covalent or other association with a radionuclide carbonyl or Tc (I) or and Tc(V) ligand. Examples of metal chelating agents include a substituted or unsubstituted $N_2S_2$ structure, a $N_4$ structure, an isonitrile, a hydrazine, a triaminothiol, a chelating agent with a hydrazinonicotinic acid group, a phosphorus group, phosphinothiols, thioesters, thioethers, a picolineamine monoacetic acid, a pyridine or bipyridyl based compound, and a substituted or unsubstituted cyclopentadienyl. Some examples of low oxidization state metals include metals with an oxidation state less than or equal to about 4, for example Tc(I), Re(I), and Cu(0).

Metallic carbonyl ligands of the present disclosure include radioisotopic gallium, indium and copper (e.g. $^{68}$Ga, $^{67}$Ga, $^{111}$In, $^{62}$Cu, $^{64}$Cu) in addition to technetium ($^{99m}$Tc) and rhenium. The properties of the Group VII metals technetium and rhenium are very similar due to their periodic relationship. It is anticipated that the metals will demonstrate similar reaction chemistry, which is often the case for the thiol, nitrogen, and oxo-chemistry of these two metals. Likewise, perrhenate and pertechnetate have very similar reaction behaviors. The similar reductions of the M(VII) oxo species allow for easy substitution of the nonradioactive rhenium as a model for the medicinally useful technetium-99m, which routinely uses reduced $^{99m}$TcO$_4$.

In another aspect, the imaging agent comprises the compound represented by the formula:

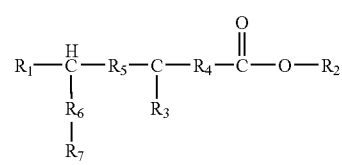

(2)

wherein $R_1$, $R_4$, $R_5$, and $R_6$ are each independently selected from an alkyl, alkenyl or a bond;

$R_2$ is selected from the group consisting of a hydrogen, a primary amine, a secondary amine, a tertiary amine, an alkyl group, a substituted alkyl group, an aryl group, and a substituted aryl group;

$R_3$ is selected from the group consisting of a hydrogen, an alkyl, a hydroxyl, a keto ester, an alkoxy, a halide, and an amine;

$R_7$ is selected from:

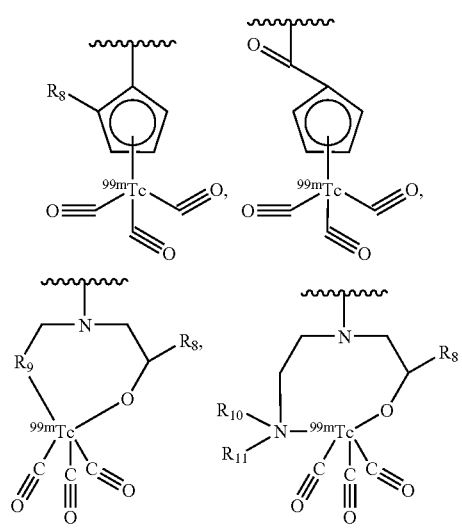

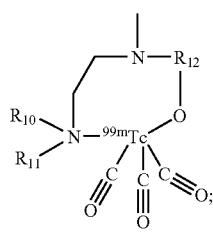

$R_8$ is selected from the group O, H, OH, alkoxy, or O-alkyl;

$R_9$ is any heterocycle;

$R_{10}$ and $R_{11}$ are each independently hydrogen, alkyl or substituted alkyl;

$R_{12}$ is selected from the group of aryl, alkyl, or heterocycle; the stereochemical configuration of a compound represented by 2 may be R or S, at the stereocenters; or a mixture of these configurations, and the pharmaceutically acceptable salts, esters, amides, and prodrugs thereof.

In one embodiment, the compound 2 is a R stereoisomer of more than about 75% isomeric purity. In another embodiment, the compound 2 is a S stereoisomer of more than about 75% isomeric purity.

In an embodiment, $R_3$ is selected from a methyl group or a substituted methyl group. In another embodiment R3 is $CH_3$ or $CF_3$. In another embodiment, $R_3$ is bound to the C-3 position relative to the carboxyl end of compound 2. In yet another embodiment, $R_3$ is bound to the C5, C7, or C9 position.

In another embodiment, $R_8$ is O.

In another aspect, the disclosure provides an imaging agent comprising the compound represented by:

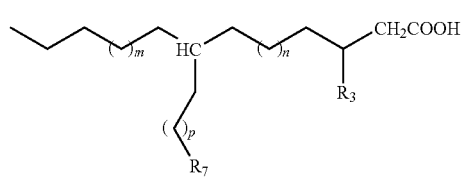

wherein $R_3$ is H or alkyl;

$R_7$ is selected from

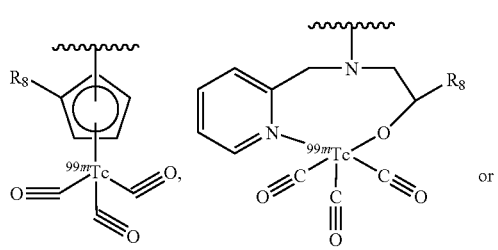

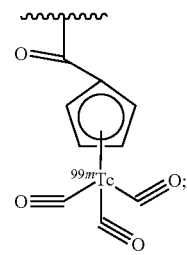

$R_8$ is selected from the group O, H, OH, alkoxy, or O-alkyl;

m is an integer between 0 and 12 inclusive;

n is an integer between 0 and 12 inclusive;

p is an integer between 0 and 12 inclusive; and the stereochemical configuration of a compound represented by 3 may be R or S, at the stereocenters; or a mixture of these configurations, and the pharmaceutically acceptable salts, esters, amides, and prodrugs thereof.

In an embodiment, a composition is provided that comprises compound 3; wherein the compound is a R stereoisomer, and the composition is of more than about 75%, more than about 80%, or even more than about 90% isomeric purity. In another embodiment, a composition is provided that comprises compound 3; wherein the compound is a S stereoisomer, and the composition is of more than about 75% more than about 80%, or even more than about 90% isomeric purity. In an exemplary embodiment, the purity of composition comprising a stereoisomer is such that the desired heart to blood ratio, or heart intake, is obtained.

In one embodiment, $R_8$ is O.

In another aspect, the imaging agent comprises a compound represented by the formula:

wherein $R_7$ is selected from

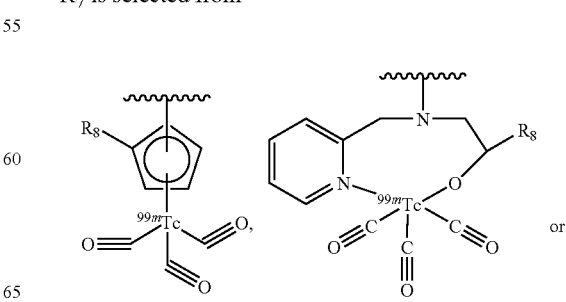

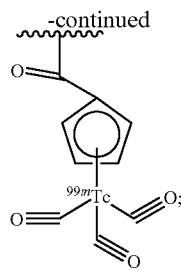

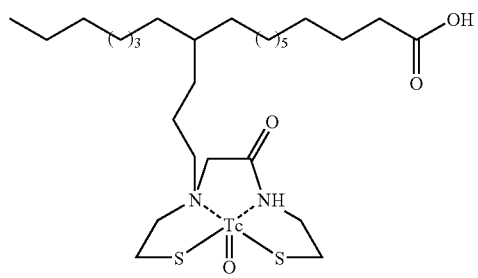

C18P.MAMA

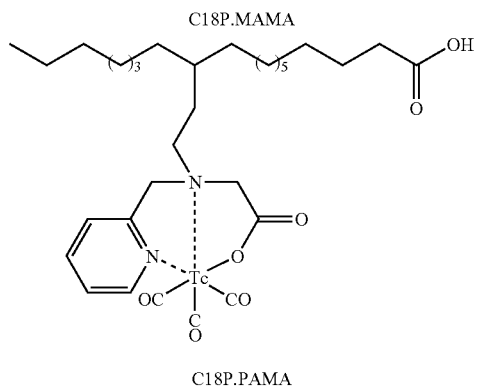

C18P.PAMA $R_8$ is selected from the group O, H, OH, alkoxy, or O-alkyl;

m is an integer selected from 0 to 12;

p is an integer selected from 0, 1, 2, 4, 6 or 8; and the stereochemical configuration of a compound represented by 4 may be R or S, at the stereocenters; or a mixture of these configurations, and the pharmaceutically acceptable salts, esters, amides, and prodrugs thereof.

In one embodiment, m is an integer selected from 0, 1 or 2. In another embodiment, $R_8$ is O.

In an embodiment, the compound 4 is a R stereoisomer of more than about 75% isomeric purity. In another embodiment, the compound 4 is a S stereoisomer of more than about 75% isomeric purity.

In one embodiment, the compounds of the present disclosure have high specificity for the myocardium when administered to a subject in vivo. In one embodiment, the fatty acid complex may show a heart-to-blood ratio of at least about 3 to 1, at least about 6 to 1. In one embodiment, the fatty acid complex may show a heart retention rate of at least 0.5% ID/g within about 60 min of administration.

Compounds of the present disclosure that contain a beta-methyl group may have a higher retention of radioactivity and may prevent in vivo beta-oxidation from occurring on the molecule and thus prolong myocardial retention of the Tc-fatty acid. In one embodiment, the chain length of fragment A will remain constant.

The chain length of the fatty acid may have a dramatic effect on heart uptake. Addition of a Tc-chelator moiety and a carbon linker to the fatty acid also may have an effect on the overall lipophilicity of the molecule; however, it is not clear how this change influences the transport of the fatty acid into myocardial cells. In one embodiment, the relationship between chain length and chelating group may be optimized by varying the length of the fatty acid backbone from C-16 to C-20. This structural variation, shown by fragment B, may be accomplished synthetically by using alkyl bromides of different carbon lengths.

Attaching the Tc-metal core via a carbon linker to the fatty acid may minimize transport interference into myocardial cells. In fragment C, (FIG. 1) the carbon spacer may be lengthened from m=2, to m=4 and 6 to determine if moving the metal cluster further away from the fatty acid backbone may improve heart accumulation.

In one embodiment, the type of metal core on the fatty acid influences the heart-to-blood ratio. Since attachment of the chelator to the fatty acid is performed synthetically in the last remaining steps, other chelate moieties may be used. These chelators, represented by fragment D, will include the PAMA (picolineamine monoacetic acid), MAMA($N_2S_2$) ligands, and cyclopentadienyl ligands. For example, representative compounds may be:

The Tc-cyclopentadienyl system (Cp) may be prepared by methods known in the art. The overall size of this Tc-complex is smaller than the Tc-PAMA, and importantly, Tc-Cp does not contain nitrogen atoms, which may influence lung accumulation.

Synthesis of fragment A containing the beta-methyl group may be done using a modified approach. This route involves preparing 2-methyloctanoic acid 8-trityl ether and then converting the alpha-methyl carboxylic acid to 3-methyl-nonanoic acid 9-trityl ether via hydrolysis of a nitrile intermediate.

Attachment of alkyl chain B to the beta-methyl fragment A may comprise use of a Grignard addition, prepared from the appropriate alkyl bromide, to the aldehyde of A. Oxidation of the resultant alcohol furnishes the ketone, which can now undergo nucleophilic addition of a lithium acetylide to give the tertiary alcohol. Dehydration of the product using methane sulfonyl chloride and base affords the enyne. Removal of the trityl group using p-toluene sulfonic acid in methanol gives the alcohol, which is then oxidized by Jones' Reagent to the carboxylic acid. Hydrogenation of the corresponding methyl ester and bromination of the resultant alcohol provides the bromo methyl ester. The chelate moiety is now attached to the bromo-pendant fatty acid ester. The two stereogenic centers created in the molecule will produce a mixture consisting of two diasteromers which may be separated by HPLC.

The $^{99m}$Tc-labeled fatty acids may be synthesized using a standard $^{99m}$TcO$_4$− reduction with tin dichloride, as well as, employing the convenient [$^{99m}$Tc(CO)$_3$(H$_2$O$_3$)]+ precursor.

The $^{99m}$Tc (I) precursor may be prepared from $^{99m}$TcO$_4$− in saline and CO at normal pressure.

Pharmacokinetic characterization was accomplished by radiometric analysis of heart, blood, lung, kidney, liver and other tissue at various times following administration of the 99mTc-labeled fatty acid analogs to rats. A comparison of heart uptake and pharmacokinetic characteristics of the 99mTc-fatty acids with those of [I-123]-(15-p-iodophenyl)- methylpentadecanoic acid (I-BMPPA) was performed in Sprague Dawley rats (male, 90-130 grams). Six new compounds were evaluated at up to four time points each (5, 15, 60, and 120 minutes) with a minimum of three animals per time point. Non-anesthetized animals were injected with 20-50 µCi in 100 µl via the tail vein and sacrificed at increasing time points post injection. The organs were excised and counted in a gamma counter. Experiments were also conducted to compare the effects of injection media using 10% ethanol, 10% bovine serum albumin and 7% ursodeoxycholic acid on distribution.

The nature of the injection media was found to have a significant effect on the heart uptake of BMIPP with ethanol showing almost 75% less in the heart than observed with ursodeoxycholic acid. Consequently, compounds were studied with various media to screen out effects of the solublizing agent. The 99mTc-labeled C18P.MAMA appears to have the greatest heart accumulation (Table 1); however, this value is distorted by the high blood retention. The iodinated agent BMIPP has high extraction into the heart but slow blood clearance with gradual washout from the heart, liver and kidneys. The 99mTc-labeled C18P.PAMA shows a maximal heart accumulation of about 0.36% per organ at 30 minutes decreasing to 0.13% at 60 minutes. By contrast the clinical agent 123I-BMIPP gives an uptake in the heart of 3.49 and 1.62 percent per organ at 15 and 60 minutes, respectively, in the rat. The myocardial clearance rate is greater for C18P.PAMA, which does not have a beta-methyl group to inhibit metabolism. The more rapid clearance of these two compounds compared to humans could be due to higher metabolic rates or increased beta-oxidation in the rat.

synthetase and diacylglycerol acyltransferase were similar in heart tissue from wild type and CD 36 knock out mice. This transporter membrane may also represent an important control site for fatty acid metabolism in vitro by regulating fatty acid esterification at the level of diacylglycerol acyltransferase by determining fatty acyl-CoA supply.

4. Dosage and Administration

The imaging agents of the disclosure may be used in accordance with the methods of the disclosure by those of skill in the art, e.g., by specialists in nuclear medicine, to image cardiovascular tissue in a mammal or to detect cardiovascular lesions in a mammal. Some cardiovascular lesions are evident when a dark spot appears within the image, for example, within a labeled heart, indicating the presence of necrotic tissue. Alternatively, a carcinomic lesion might be detectable as a brighter spot within the image, indicating a region of enhanced metabolism at the site of a tumor. A particularly useful imaging approach employs more than one imaging agent to perform simultaneous studies. For example, simultaneous studies of perfusion and metabolic function would allow study of coupling and uncoupling of flow and metabolism, thus facilitating determinations of tissue viability after a cardiac injury. Such determinations may be useful in diagnosis of cardiac ischemia, cardiomyopathy, tissue viability, hybrinating heart, and other heart abnormalities.

The imaging agents of the disclosure may be used in the following manner. An effective amount of the imaging agent (from 1 to 50 mCi) may be combined with a pharmaceutically acceptable carrier for use in imaging studies. In accordance with the disclosure, "an effective amount" of the imaging agent of the disclosure is defined as an amount sufficient to

TABLE 1

Percent injected dose per gram of Tc-99m agents in the rat at 15-min post injection.

|  | BMIPP | P.PAMA | P.MAMA | I.PAMA | T.PAMA | T.MAMA |
|---|---|---|---|---|---|---|
| Blood | 1.30 ± 0.19 | 0.09 ± 0.02 | 1.56 ± 0.17 | 0.07 ± 0.01 | 0.32 ± 0.13 | 0.20 ± 0.04 |
| Heart | 4.60 ± 0.63 | 0.34 ± 0.06 | 0.66 ± 0.11 | 0.03 ± 0.01 | 0.31 ± 0.0 | 0.13 ± 0.02 |
| Lung | 1.83 ± 0.22 | 0.34 ± 0.08 | 0.97 ± 0.14 | 0.05 ± 0.01 | 0.26 ± 0.06 | 0.15 ± 0.08 |
| Liver | 2.97 ± 0.56 | 3.91 ± 0.61 | 1.17 ± 0.13 | 0.39 ± 0.07 | 6.80 ± 3.38 | 1.38 ± 0.20 |
| Kidneys | 4.09 ± 0.82 | 0.37 ± 0.04 | 3.76 ± 0.44 | 0.63 ± 0.06 | 2.71 ± 1.38 | 2.28 ± 0.29 |

Figure 3:
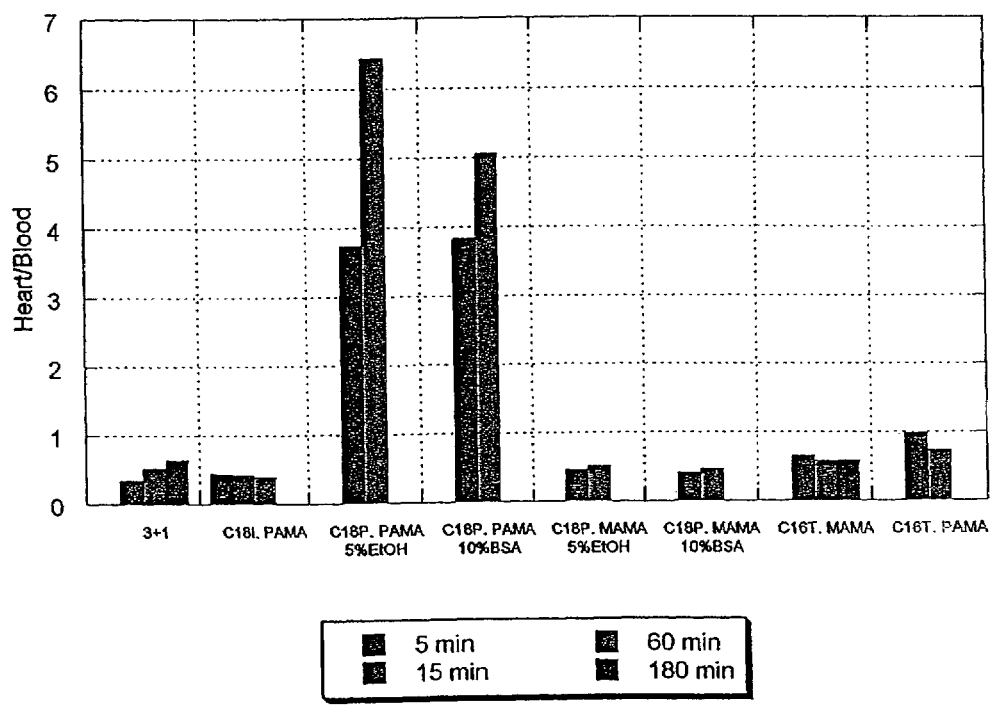
FIG. 3 shows a comparison of heart/blood ratios for compounds of the present disclosure.

Even with its greater accumulation in the heart, the heart-to-blood ratio for BMIPP, an indicator of image resolution, is only 2.2 and 1.6 at 15 and 60 minutes compared with 4.8 and 5.1 for C18P.PAMA. FIG. 3 shows a comparison of heart/blood ratios for some Tc compounds. The liver activity goes from 19.7 to 7.2 percent per organ in 45 minutes for BMIPP and from 32.3 to 5.1 for the C18P.PAMA during the same period indicating better target to background ratios for the surrounding organ.

The type and position of the technetium metal core on the fatty acid may have an effect on heart accumulation and blood clearance. Attaching the Tc-metal core via a carbon linker to the fatty acid apparently may minimize interference with transport into myocardial cell. The heart retention of C18P.PAMA and C18P.MAMA gradually decreased with time, slower than blood clearance, which can mean they are undergoing beta-oxidation as a normal fatty acid.

Knock-out mice may be used to analyze the radiolabeled fatty acids. To date, investigators have depended on heart-to-blood ratios and uptake in the heart as markers of fatty acid behavior. The transmembrane protein CD36 has been identified in isolated cell studies as a putative transporter of long chain fatty acids. Key enzymes such as long chain acyl-CoA yield an acceptable image using equipment which is available for clinical use. An effective amount of the imaging agent of the disclosure may be administered in more than one injection. Effective amounts of the imaging agent of the disclosure will vary according to factors such as the degree of susceptibility of the individual, the age, sex, and weight of the individual, idiosyncratic responses of the individual and dosimetry. Effective amounts of the imaging agent of the disclosure will also vary according to instrument and film-related factors. Optimization of such factors is well within the level of skill of a person skilled in the art.

As used herein, "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. The imaging agent of the disclosure may further be administered to an individual in an appropriate diluent or adjuvant, co-administered with enzyme inhibitors or in an appropriate carrier such as human serum albumin or liposomes. Supplementary active compounds can also be incorporated into the imaging agent of the disclosure. Pharmaceutically acceptable diluents; include saline and aqueous buffer solutions. Adjuvants contemplated herein include resorcinols, non-ionic surfactants such as polyoxyethylene oleyl ether and nhexadecyl polyethylene ether. Enzyme inhibitors include pancreatic trypsin inhibitor, diethylpyrocarbonate, and trasylol. Liposomes include water-in-oil-in-water CGF emulsions as well as conventional liposomes (Strejan et al. (1984) *J. Neuroimmunol.* 7, 27).

In one embodiment, the imaging agent of the disclosure is administered parenterally as injections (intravenous, intramuscular or subcutaneous). The imaging agent may be formulated as a sterile, pyrogen-free, parenterally acceptable aqueous solution. The preparation of such parenterally acceptable solutions, having due regard to pH, isotonicity, stability, and the like, is within the skill in the art. Certain pharmaceutical compositions of this disclosure suitable for parenteral administration comprise one or more imaging agents in combination with one or more pharmaceutically acceptable sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. A formulation for injection should contain, in addition to the cardiovascular imaging agent, an isotonic vehicle such as sodium chloride solution, Ringer's solution, dextrose solution, dextrose and sodium chloride solution, lactated Ringer's solution, dextran solution, sorbitol solution, a solution containing polyvinyl alcohol, or an osmotically balanced solution comprising a surfactant and a viscosity-enhancing agent, or other vehicle as known in the art. The formulation used in the present disclosure may also contain stabilizers, preservatives, buffers, antioxidants, or other additives known to those of skill in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

5. Kits

In another embodiment, the disclosure provides a kit for imaging which comprises one or more of the imaging agents described above, in combination with a pharmaceutically acceptable solution containing a carrier such as human serum albumin or an auxiliary molecule such as mannitol or gluconate. Human serum albumin for use in the kit of the disclosure may be made in any way, for example, through purification of the protein from human serum or through recombinant expression of a vector containing a gene encoding human serum albumin. Other substances may also be used as carriers in accordance with this embodiment of the disclosure, for example, detergents, dilute alcohols, carbohydrates, and the like. In one embodiment, a kit according to the disclosure may contain from about 1 to about 30 mCi of an imaging agent. In another embodiment, a kit may contain the unlabeled fatty acid stereoisomer which has been covalently or non-covalently combined with a chelating agent, and an auxiliary molecule such as mannitol, gluconate, and the like. The unlabeled fatty acid stereoisomer/chelating agent may be provided in solution or in lyophilized form. The radionuclide, for example, $^{99m}$Tc from a commercially available $^{99}$Mo/$^{99m}$Tc generator, is combined with the unlabeled fatty acid stereoisomer/chelating agent for a time and at a temperature sufficient to chelate the radionuclide to the fatty acid stereoisomer/chelating agent, and the imaging agent thus formed is injected into the patient. The kits of the disclosure may also include other components which facilitate practice of the methods of the disclosure. For example, buffers, syringes, film, instructions, and the like may optionally be included as components of the kits of the disclosure.

EXEMPLIFICATION

The disclosure now being generally described, it will be more readily understood by reference to the following examples which are included merely for purposes of illustration of certain aspects and embodiments of the present disclosure and are not intended to limit the disclosure.

Example 1

Synthesis of $[^{99m}Tc(CO)_{3\eta3}$-(Fatty Acid PAMA or Cp)] Derivatives.

Carbon monoxide is flushed for 20 minutes into a sealed vial containing 18 mg each of $Na_2CO_3$ and $NaBH_4$. Added to the pressurized vial is 1 ml of $TcO_4^-$ and the solution is heated at 100° C. for 30 minutes. After cooling the solution, formation of $[Tc(CO)_3(H_2O)_3]^+$ is examined by HPLC. The $[Tc(CO)_3(H_2O)_3]^+$ elutes at 3 minutes while unreacted $TcO_4^-$ has a retention time of 8 minutes. Utilizing the method described for the synthesis of $[99mTc(CO)_3(H_2O)_3]^+$, 2 mg of the appropriate fatty acid derivative is added to the dry vial before introducing the $Na_2CO_3$ and $NaBH_4$. The mixture is incubated at 100° C. for 30 minutes, whereupon it is filtered and analyzed via HPLC for product yield and purity.

Example 2

Synthesis of $[^{99m}TcO$-(Fatty Acid MAMA)] Derivatives.

Preparation of the Tc-99m-labeled MAMA and DADT derivatized fatty acid complexes is achieved by adding 500 ul of a Tc-99m-glucoheptate kit (Dupont) to a solution of the appropriate derivatized fatty acid (2 mg/100 ul methanol) and 100 ul of DMSO. The mixture is incubated at 100° C. for 30 minutes, whereupon it is filtered through a Millipore Millex-GV 0.22 μm filter and analyzed via HPLC for product yield and purity. The radioactive product(s) elutes at >18 minutes.

Example 3

Preparation of C18 Pendant PAMA

Methyl 9-(1-bromopropane)octadecanoate (0.6 g, 1.4 mmol), N-(2-methyl acetate) 2-aminomethyl pyridine (0.42 g, 2.1 mmol), and potassium carbonate (0.05 g) were stirred in DMF (10 mL) at 110-120 C for 2 hrs. The mixture was diluted with methylene chloride (50 mL) washed with water (3×) and dried. Chromatography on silica gel (95:5 hexane/ethyl acetate) afforded 0.3 g (43%) of the diester.

Example 4

Preparation of [Re(CO)$_3$(Fatty Acid PAMA)]

Figure 4:
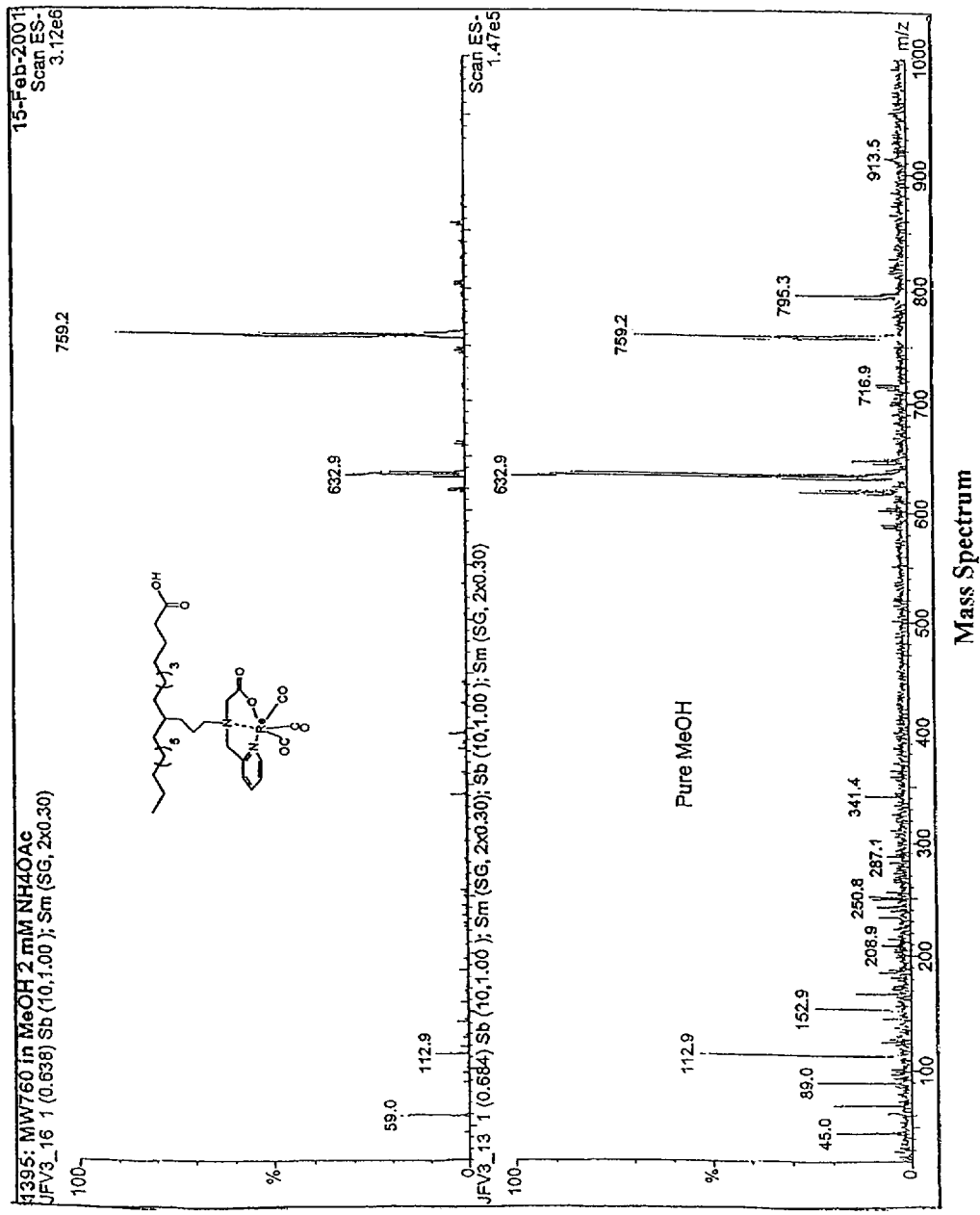
FIG. 4 shows a mass spectrum for a compound of the present disclosure.

In a 100 mL flask is placed [NEt$_4$][ReBr$_3$(CO)$_3$] (0.053 g, 0.0680 mmol) in 10 mL of distilled water. To the stirring solution is added the pendant PAMA acid (0.040 g, 0.0816 mmol) in 1 mL of methanol. The solution immediately changed its appearance from clear and colorless to cloudy white upon addition. The reaction mixture is heated at 80° C. for 4 hours then stirred at room temperature for 12 hours. After being evaporated to dryness the mixture is purified using a silica column (10% methanol:90% methylene chloride). The resulting product was dissolved in methanol and analyzed by mass spectroscopy, with a MW of 759.2. (FIG. 4)

Example 5

Preparation of [ReO(Fatty Acid MAMA)].

In a 100 mL flask is placed [ReOCl$_3$(PPh$_3$)$_2$] (0.050 g, 0.0600 mmol) in 10 mL of methanol. To the stirring solution is added the pendant MAMA acid (0.034 g, 0.0661 mmol) in 1 mL of methanol. The solution immediately changed its appearance from cloudy green to brown upon addition of triethylamine (0.012 g, 0.120 mmol). The reaction mixture is refluxed for 4 hours then vacuumed to dryness. The mixture is purified using a silica column (20% acetone:80% chloroform).

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, parameters, descriptive features and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference are the following:

PUBLICATIONS

Alberto, R. *J. Label. Cpd. Rad.* 2001, 44, 54-6; ibid. Lee, BC. 535-7; Knapp et al *J. Med. Chem.* 1984, 27, 390-7; Schubiger *J. Am. Chem. Soc.* 1998, 120, 7987-8.

We claim:
1. The imaging agent represented by the structure 3:

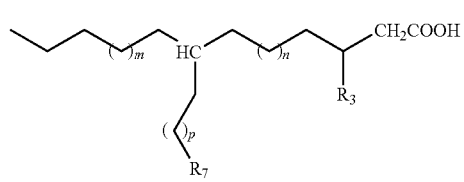

wherein R$_3$ is H or alkyl;
R$_7$ is

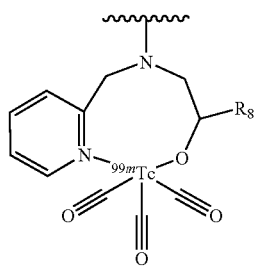

wherein the wavy line indicates the point of attachment to the rest of the molecule;
R$_8$ is selected from the group consisting of =O (oxo), H, OH, alkoxy, or O-alkyl;
m is an integer between 0 and 12 inclusive;
n is an integer between 0 and 12 inclusive;
p is an integer between 0 and 12 inclusive; wherein a stereochemical configuration of a compound represented by 3 may be R or S, at the stereocenters; or a mixture of these configurations;
or a pharmaceutically acceptable salt or amide thereof.
2. The imaging agent of claim 1, wherein R$_8$ is =O (oxo).
3. A composition comprising the imaging agent of claim 1, wherein the stereochemical configuration of the imaging agent is a R-stereoisomer, and the composition is of more than about 75% isomeric purity.
4. A composition comprising the imaging agent of claim 1, wherein the stereochemical configuration of the imaging agent is a S-stereoisomer, and the composition is of more than about 75% isomeric purity.
5. The imaging agent represented by the structure 4:

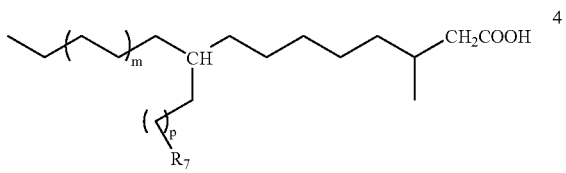

wherein
R$_7$ is

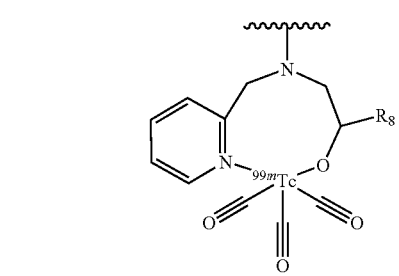

wherein the wavy line indicates the point of attachment to the rest of the molecule;
R$_8$ is selected from the group consisting of =O (oxo), H, OH, alkoxy, or O-alkyl;
m is an integer selected from 0 to 12;
p is an integer selected from 0, 1, 2, 4, 6 or 8, wherein a stereochemical configuration of a compound represented by structure 4 may be R or S, at the stereocenters; or a mixture of these configurations;

or a pharmaceutically acceptable salt or amide thereof.

6. The imaging agent of claim 5, wherein m is selected from 0, 1, or 2.

7. A composition comprising the imaging agent of claim 5, wherein the stereochemical configuration of the imaging agent is a R-stereoisomer, and the composition is of more than about 75% isomeric purity.

8. A composition comprising the imaging agent of claim 6, wherein the stereochemical configuration of the imaging agent is a S-stercoisomer, and the composition is of more than about 75% isomeric purity.

* * * * *